US00PP08839P

United States Patent [19]

Meilland

[11] Patent Number: Plant 8,839

[45] Date of Patent: Jul. 19, 1994

[54] ROSE PLANT — MEIPELTA VARIETY

[75] Inventor: Alain A. Meilland, Antibes, France

[73] Assignee: The Conard-Pyle Company, West Grove, Pa.

[21] Appl. No.: 119,371

[22] Filed: Sep. 10, 1993

[51] Int. Cl.[5] ..... A01H 5/00

[52] U.S. Cl. ..... Plt./1

[58] Field of Search ..... Plt. 1, 26, 27, 28, Plt. 22

*Primary Examiner*—Howard J. Locker

*Attorney, Agent, or Firm*—Burns, Doane, Swecker & Mathis

[57] ABSTRACT

A new and distinct variety of shrub rose plant having a spreading ground cover growth habit is provided which forms attractive long-lasting half-double blossoms that are Rose Bengal suffused with Neyron Rose in coloration. The blossoms commonly are formed very abundantly and continuously and possess firm petals which detach cleanly. The vegetation is vigorous. The new variety is not particularly affected by cryptogamic diseases, and possesses good resistance to frost. Attractive ornamentation for growing in the landscape is provided by the new variety.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) was the Meitiraca variety (non-patented in the United States). The male parent (i.e., the pollen parent) of the new variety was the Meimont variety (non-patented in the United States). The parentage of the new variety can be summarized as follows:

Meitiraca × Meimont.

The seeds resulting from the above pollination were sown and 11 plantlets were obtained which were physically and biologically different from each other. Selective study resulted in the identification of a single plant of the new variety.

It is found that the new variety of shrub rose plant possesses the following combination of characteristics:

(a) forms attractive half-double blossoms which are Rose Bengal suffused with Neyron Rose,
(b) forms petals which are firm and drop off cleanly,
(c) forms medium green adult wood,
(d) exhibits a prostrate growth habit,
(e) exhibits excellent disease resistance, and
(f) is particularly well suited for growing in the landscape as a ground cover.

The new variety meets the needs of the horticultural industry for many uses. It can be grown to particular advantage as attractive ornamentation in parks, gardens, public areas, and residential landscapes.

The characteristics of the new variety have been found to be homogeneous and stable and to be strictly transmissible by asexual propagation that was carried out in France (e.g., by budding, grafting, cuttage, etc.) from one generation to another.

The new variety has been named the Meipelta variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were three years of age and were grown on their own roots in the open air at Le-Cannet-des-Maures, Var, France.

FIG. 1—illustrates a specimen of a young shoot;

FIG. 2—illustrates a specimen of two floral buds before the opening of the sepals;

FIG. 3—illustrates a specimen of two floral buds as the sepals open;

FIG. 4—illustrates a specimen of two floral buds as the petals open;

FIG. 5—illustrates a specimen of two flowers in the course of blooming;

FIG. 6—illustrates a specimen of a open flower - plan view - obverse;

FIG. 7—illustrates a specimen of a open flower - plan view - reverse;

FIG. 8—illustrates a specimen of a open flower immediately prior to petal drop - plan view - obverse;

FIG. 9—illustrates a specimen of a open flower immediately prior to petal drop - plan view - reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of leaves with three leaflets - upper and under surfaces;

FIG. 15—illustrates a specimen of leaves with five leaflets - upper and under surfaces; and FIG. 16—illustrates a specimen of leaves with seven leaflets - plan view - upper and under surfaces.

DETAILED DESCRIPTION

Figures 1, 2, 3, 4, 5, 6, 7, 8, 9, 10, 11, 12, 13, 14, 15, 16:
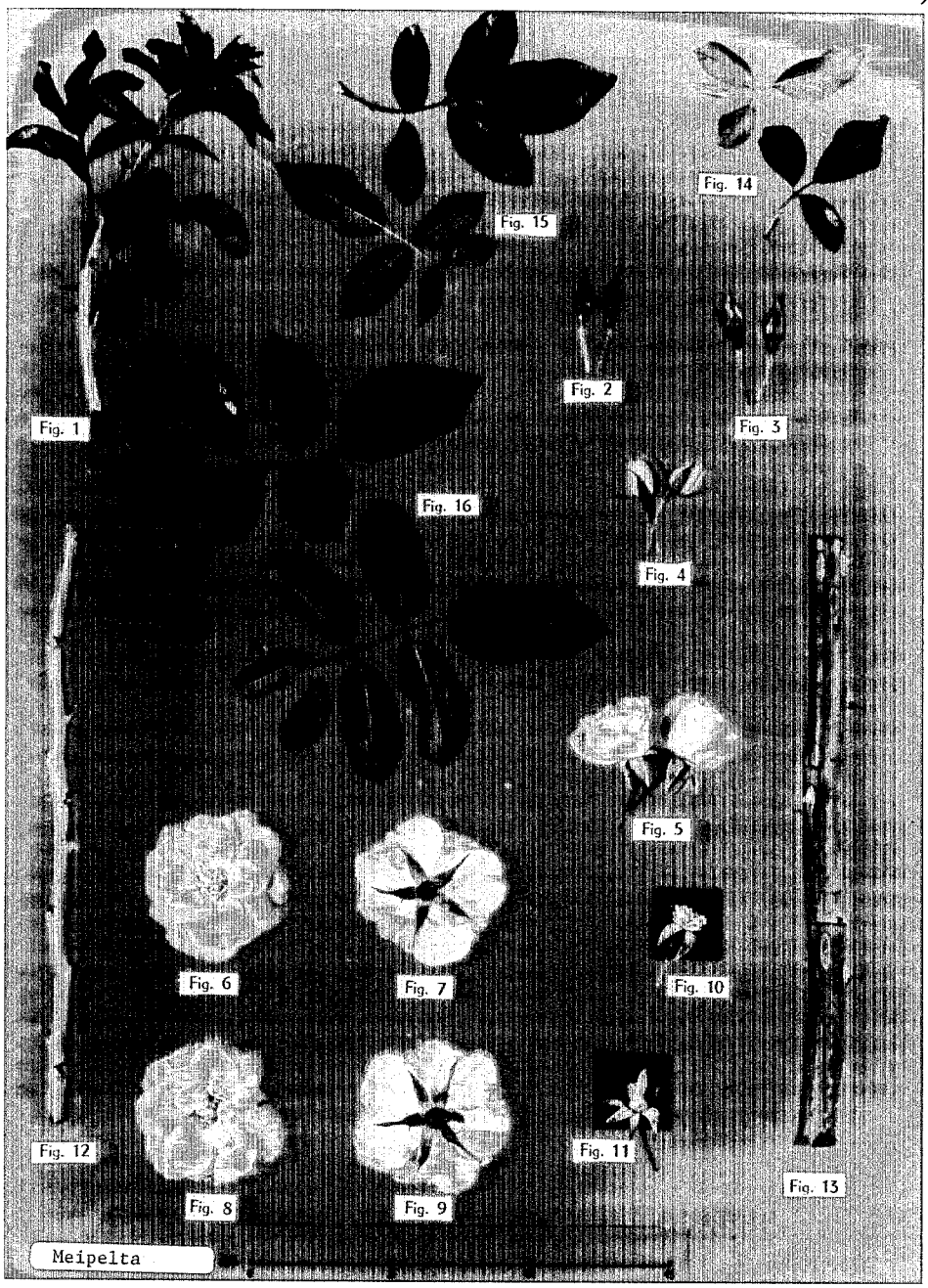

The chart used in the identification of the colors is that of the Royal Horticultural Society (R.H.S. Colour Chart). The terminology preceding the numbered reference has been added to indicate in common terms the corresponding color. The description is based on three year old specimens of the new variety while grown outdoors on their own roots at Le-Cannet-des-Maures, Var, France.

Class: Shrub.

Plant:

*Height.*—Approximately 80 to 90 cm. on average when fully mature at the end of two growing seasons when grown on its own roots.

*Habit.*—Spreading, ground cover.

Branches:

*Color.*—Young stems: lettuce green, Yellow-Green Group 144A, more or less shaded with a reddish tint. Adult wood: medium green, Yellow-Green Group 146A, more or less shaded with a reddish tint.

Leaves:

*Stipules.*—Adnate, pectinate, narrow and indented.

*Petioles.*—Upper surface: striped reddish brown on young foliage, and medium green on adult foliage with more or less glandular edges. Under surface: light green with some rarely appearing prickles.

*Leaflets.*—Number: 3, 5 (most common), and 7. Shape: oval. Serration: simple and regular. Texture: rough. General appearance: dense semi-glossy foliage. Color (young foliage): Upper surface: lettuce green, Yellow-Green Group 144A, more or less tinted with reddish coloration. Under surface: light green, Yellow-Green Group 146C more or less tinted with reddish coloration. Color (adult foliage): upper surface: deep green, Yellow-Green Group 146A. Under surface: light green, Yellow-Green Group 146C.

Inflorescence:

*Number of flowers.*—Approximately 1 to 11 flowers per stem.

*Peduncle.*—Light green, more or less tinted with reddish coloration, numerous prickles are intermingled with pendiculate glands, approximately 2 to 2.5 cm. in length on average.

*Sepals.*—Upper surface: tomentose, greenish in coloration. Under surface: the sepals have a glandular edge and are rarely appendiculated.

*Buds.*—Shape: ovoid. Length: approximately 1.5 cm. on average. Size: small. Color when opening: Upper surface: Turkey Red, Red Group 46C, suffused with Rose Bengal, Red-Purple Group 57C, with a white eye. Under surface: Cardinal Red, Red Group 53C.

*Flower.*—Form: half-double, opens as a flat cup. Diameter: approximately 4 to 5 cm. on average. Color (when opening begins): Upper surface: Turkey Red, Red Group 46C, suffused with Rose Bengal, Red-Purple Group 57C, with a white eye. Under surface: Cardinal Red, Red Group 53C. Color (when blooming): Upper surface: Rose Bengal, Red-Purple Group 57C, suffused with Neyron Rose, Red Group 55A, with a white eye. Under surface: Rose Bengal, Red-Purple Group 57C, and whitish marbled especially at the petal bases. Color (at end of opening): Upper surface: Rose Bengal, Red-Purple Group 57C, suffused with Neyron Rose, Red Group 55A, with a white eye. Under surface: Rose Bengal, Red-Purple Group 57C, and whitish marbled especially at the petal bases. Fragrance: none. Lasting quality: long on the plant. Petal form: usually oval. Texture: firm. Petal number: approximately 15 to 18 on average. Petal drop: good. Stamen number: approximately 65 on average. Anthers: normal, ochre in coloration. Filaments: bright yellow and of irregular heights. Pistils: approximately 18 to 20 on average. Stigmas: normal and located at approximately the same level as the anthers. Styles: greenish in coloration, and irregular in height. Receptacle: medium green with a reddish tint at the dehiscence of the anthers and in longitudinal section it is narrow and pear-shaped.

Development:

*Vegetation.*—Vigorous.

*Blooming.*—Very abundant and continuous.

*Aptitude to bear fruits.*—None.

*Resistance to frost.*—Good.

*Resistance to diseases.*—Good.

I claim:

1. A new and distinct variety of shrub rose plant characterized by the following combination of characteristics:

(a) forms attractive half-double blossoms which are Rose Bengal suffused with Neyron Rose,
(b) forms petals which are firm and drop off cleanly,
(c) forms medium green adult wood,
(d) exhibits a prostrate growth habit,
(e) exhibits excellent disease resistance, and
(f) is particularly well-suited for growing in the landscape as a ground cover;

substantially as herein shown and described.

* * * * *

Meipelta